US010912608B2

(12) United States Patent
Lam et al.

(10) Patent No.: US 10,912,608 B2
(45) Date of Patent: Feb. 9, 2021

(54) RADIO FREQUENCY ELECTRO-THROMBECTOMY DEVICE

(71) Applicant: The Hong Kong University of Science and Technology, Hong Kong (CN)

(72) Inventors: David Chuen Chun Lam, Hong Kong (CN); Chi Hang Chon, Hong Kong (CN); John Ching Kwong Kwok, Hong Kong (CN); Matthew Ming Fai Yuen, Hong Kong (CN); Zhen Qin, Hong Kong (CN); Alexander Ka Ngai Lam, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 564 days.

(21) Appl. No.: 15/574,758

(22) PCT Filed: Jun. 6, 2016

(86) PCT No.: PCT/IB2016/000872
§ 371 (c)(1),
(2) Date: Nov. 16, 2017

(87) PCT Pub. No.: WO2016/198947
PCT Pub. Date: Dec. 15, 2016

(65) Prior Publication Data
US 2018/0140354 A1 May 24, 2018

Related U.S. Application Data

(60) Provisional application No. 62/172,043, filed on Jun. 6, 2015.

(51) Int. Cl.
*A61B 18/12* (2006.01)
*A61B 18/14* (2006.01)
(Continued)

(52) U.S. Cl.
CPC ........ *A61B 18/1492* (2013.01); *A61B 17/221* (2013.01); *A61B 2017/22034* (2013.01);
(Continued)

(58) Field of Classification Search
CPC combination set(s) only.
See application file for complete search history.

(56) References Cited

U.S. PATENT DOCUMENTS

| 5,178,618 A | 1/1993 | Kandarpa |
| 5,286,254 A | 2/1994 | Shapland et al. |

(Continued)

FOREIGN PATENT DOCUMENTS

| CN | 101396295 A | 4/2009 |
| CN | 103841905 A | 6/2014 |

(Continued)

OTHER PUBLICATIONS

Supplementary European Search Report dated Jan. 9, 2019 in European Application No. 16806954.0.
(Continued)

*Primary Examiner* — Daniel W Fowler
(74) *Attorney, Agent, or Firm* — Saliwanchik, Lloyd & Eisenschenk

(57) ABSTRACT

A device is designed to remove blockages in a lumen such as a thrombus, blood clot, or embolus. The device comprises a manipulating wire and a structure that can conduct electrical current to a lumen blockage. The electrical current is preferably in radio frequency (RF). The RF electric current in the blockage can excite the contents such as proteins of the blockage, so that cross-linking density and interfacial adsorption of the entire blockage is enhanced. The enhanced cross-linking density can result in increased fracture resistance of the blockage such that fracture of the blockage during the removal process is unlikely. The enhanced inter-
(Continued)

facial adsorption results in increased interfacial fracture resistance between the device and blockage so that the blockage can be securely captured during the removal process without using radially applied force.

5 Claims, 4 Drawing Sheets

(51) Int. Cl.
 *A61B 17/221* (2006.01)
 *A61B 17/22* (2006.01)
 *A61B 18/00* (2006.01)
(52) U.S. Cl.
 CPC ............... *A61B 2018/0041* (2013.01); *A61B 2018/00214* (2013.01); *A61B 2018/00267* (2013.01); *A61B 2018/00398* (2013.01); *A61B 2018/00404* (2013.01); *A61B 2018/144* (2013.01); *A61B 2018/1475* (2013.01)

(56) References Cited

U.S. PATENT DOCUMENTS

| | | | |
|---|---|---|---|
| 5,904,679 A | 5/1999 | Clayman | |
| 6,071,281 A * | 6/2000 | Burnside | A61B 18/1482 606/37 |
| 6,129,698 A | 10/2000 | Beck | |
| 6,558,377 B2 * | 5/2003 | Lee | A61B 17/12022 600/381 |
| 7,749,220 B2 | 7/2010 | Schmaltz | |
| 2002/0133111 A1 | 9/2002 | Shadduck | |
| 2003/0125724 A1 * | 7/2003 | Long | A61B 18/1492 606/41 |
| 2008/0017202 A1 | 1/2008 | Michal et al. | |
| 2008/0172050 A1 | 7/2008 | Satake | |
| 2008/0262489 A1 * | 10/2008 | Steinke | A61B 18/1492 606/33 |
| 2009/0054918 A1 | 2/2009 | Henson | |
| 2011/0301594 A1 * | 12/2011 | Orion | A61B 18/1492 606/41 |

FOREIGN PATENT DOCUMENTS

| | | |
|---|---|---|
| EP | 1 707 148 A2 | 10/2006 |
| EP | 2217315 B1 | 5/2012 |
| WO | WO-2012/162437 A1 | 11/2012 |
| WO | WO-2014/079148 A1 | 5/2014 |
| WO | WO-2015/070147 A1 | 5/2015 |

OTHER PUBLICATIONS

International Search Report in International Application No. PCT/IB2016/000872, filed Jun. 6, 2016.

* cited by examiner

RADIO FREQUENCY ELECTRO-THROMBECTOMY DEVICE

CROSS-REFERENCE TO RELATED APPLICATIONS

This application is the U.S. national stage application of International Patent Application No. PCT/IB2016/000872, filed Jun. 6, 2016, which claims priority to U.S. Application No. 62/172,043, filed Jun. 6, 2015, the disclosures of each of which are incorporated herein by reference in their entirety.

BACKGROUND OF THE INVENTION

Blockage-related diseases such as ischemic stroke in different organs, including the brain and the heart, are common causes of death. A blockage in a vessel lumen, which can be a thrombus, blood clot or embolus, can lower blood perfusion of the downstream tissues. A thrombosis is the formation or presence of a thrombus or blood clot inside a blood vessel or cavity of the heart. There are two main components of a thrombus, aggregated platelets that form a platelet plug and a mesh of cross-linked fibrin protein. Although a thrombus is a healthy response to injury intended to prevent bleeding, a thrombus can become harmful in thrombosis when blot clots obstruct blood flow through healthy vessels. An embolus is a thrombus or blood clot that moves through the blood stream until it lodges in a narrowed vessel and blocks blood circulation. If the perfusion is below a certain level, cells receive insufficient amount of oxygen and will perish if the situation is prolonged. A venous embolus travels to the right side of the heart and through the pulmonary artery and leads to pulmonary embolism, while an arterial embolus can occlude any artery or arteriole downstream of the thrombus formation and can lead to cerebral stroke, myocardial infarction, or infarction in any other organ.

The pathogenesis of thrombus formation can include endothelial injury, caused, for example, by trauma or atheroma (accumulation of degenerative material in the inner layer of the artery wall consisting mostly of macrophage cells and debris containing cholesterol and fatty acids, calcium and variable amount of fibrous connective tissue); abnormal blood flow due to stasis in veins; turbulence in arteries; and hypercoaguability of the blood.

Current medical treatments for removing blockage in blood vessels, such as in cerebral blood vessels, are chemical thrombolysis and mechanical thrombectomy. Chemical thrombolysis achieves some success in acute ischemic stroke, but because of the high risk of side effects, such as symptomatic intracerebral hemorrhage (sICH), and limited treatment time window, only 10% of patients are eligible for the treatment. In addition, chemical thrombolysis when applied alone has low recanalization rates and often requires continuous treatment for up to one week. Mechanical thrombectomy has a longer treatment time window, higher recanalization rates and a lower risk of side effects. However, complications such as blockage fragmentation with the risk of distal embolization and vascular damage that can cause restenosis are major concerns.

Several drug delivery devices have been used for chemical thrombolysis with varying successes. For example, a device featuring a membrane configuration with no drug loaded in the membrane but drug delivered continuously at unknown dosage from outside the subject via a catheter to the balloon cavity where the drug passes across the balloon surface (U.S. Pat. No. 5,286,254 to Shapland et al.) failed to provide recanalization during the treatment leaving cells downstream of the blockade in oxygen deprivation. Tube systems have been employed, for example, for intracoronary thrombolysis to deliver drugs locally. However, the continuous infusion and removal of drug renders control of drug dosage difficult. A metal stent device without membrane delivering a drug through the guidewire (EP2217315B1 to Fulkerson et al.) similarly failed to allow precise control of drug dosage. Other devices have been designed to deliver drugs exclusively to the vessel portion distal of an obstruction in order to prevent reperfusion injury (e.g. US 20080017202 by Michael et al.), leaving the obstruction-causing blood clot undissolved and necessitating an additional device such as, for example, a combined balloon-stent recanalization device. Beside the difficulty of controlling drug dosages delivered utilizing any of these devices, drug delivery cannot be restricted to certain localizations. In addition, thrombolytic recanalization is not effective in all cases, might require an extended time of treatment, and often has to be combined with mechanical means of blockage removal.

Commonly used devices for mechanical removal of blockages, such as proximal devices and stent retrievers, use aspiration or radial force to capture and remove the blockage from lumen. These devices lack bulk strengthening function and interfacial strengthening function may lead to blockage fragmentation. Devices that use radial force to capture the blockage may lead to vascular damages. Other patented methods for mechanical removal of blockages include radiofrequency (RF), thermal, and ultrasound. For example, one device employs a metal stent with a heat generator (U.S. Pat. No. 5,178,618 to Kandapar et al.) to first recanalize vessels by balloon-mediated stent expansion followed by the heating of balloon and stent to 50-100° C. to kill smooth muscle cells thought to cause restenosis. However, such device does not allow the removal of material and leaves the heated clot in the vessel.

Radiofrequency (RF) has been used in percutaneous systems to ablate tissue or blockages (e.g. U.S. Pat. No. 7,749,220 to Schmaltz; U.S. Pat. No. 5,904,679 to Clayman); emulsify blockages (e.g. U.S. Pat. No. 6,129,698 by Beck; US2002133111A1 by Shadduck); or heat the inside of a balloon (e.g. US2008172050 by Satake) to cauterize a treatment site. In one example, electrodes connected to an electrosurgical generator are placed against or within a blockage and a capture element such as a filter or cage spanning the entire lumen of the vessel is positioned distal of the blockage ('220 to Schmaltz). An effective amount of energy delivered to the electrodes for an effective amount of time ablates the blockage and the capture element prevents embolization of blockage fragments. However, the blockage is not strengthened during the procedure and the efficient removal of the entire blockage depends on the complete capture of embolizing fragments in the filter/cage, whereby the size of the filter or cage must be selected appropriately to contain the entire volume of the ablated blockage material, due to the inability to perform the procedure in multiple steps.

Radio frequency has also been used to cut tissue employing a cutting element located on the exterior of a dilatable balloon ('679 to Clayman). However such device finds mainly usage in dilation of non-vascular conduits. Emulsification and extraction of blockage material with RF and laser employing, for example, a deflected fluid jet ('698 by Beck) and/or a pressure differential created between spaced RF emitters have been used whereby the energy emitted to a fluid media causes cavitation within the fluid media ('111 by Shadduck). Although the latter methods allow sequential retrieval of material dislodged from a thrombus or embolus, the devices have no effect on the stability or lack thereof of the thrombus and/or embolus material remaining as the removal procedure progresses. Since blockage destabilization by progressive removal of blockage material can cause the blockage to embolize into downstream vascular beds, a need exists for a device that can stabilize the thrombus and/or embolus during the removal procedure and prevent blockage fragmentation and embolization.

Devices that add electro-resistive heating to the wire can strengthen the solids immediately adjacent around the wire. However, the heating is non-uniform and diminishes as a function of distance away from the wire, such that the strengthening of materials at the periphery would require high heat at the wire, which may damage the nearby vessel wall.

Instead of using heat conduction as a method to strengthen the blockage, the device of the present invention conducts RF electric current to the blockage. The RF electric current can be conducted through the entire blockage so that the strengthening is more uniformly distributed without significant risk of damage to the vessel wall. Disclosed is a method of using the device of the present invention in lumen blockage removal involving navigating the device to the site of occlusion using conventional guidewire and catheter systems; deploying the device; transmitting RF electric current to the blockage; and retrieving the blockage.

BRIEF SUMMARY OF THE INVENTION

The present invention provides a device for vascular lumen blockage removal with a low risk of vessel wall damage and blockage fragmentation due to the use of RF electric current to strengthen the blockage and the blockage-device interface prior to blockage removal. Unlike conventional devices which may result in blockage fragmentation and vascular damage, the device of the present invention can minimize these problems by applying a RF electric current to a blockage, which RF electric current stabilizes the blockage and enhances adhesion between the device and the blockage. Applying RF electric current can also strengthen a blockage by increasing cross-linking density of the blockage and strengthen blockage-device interface.

Embodiments of the RF electro-thrombectomy device are designed to immediately recanalize a blocked blood vessel, minimize blockage fragmentation, and minimize vascular damage. The RF electro-thrombectomy device conducts electrical current, such as RF electric current, to pass through a blockage in a vessel lumen, such as a thrombus, blood-clot or embolus and increases the cross-linking density of components of the blockage, which increased cross-linking density increases the fracture resistance of the blockage itself and increases the interfacial fracture resistance between the device and the blockage.

DESCRIPTION OF DRAWINGS

FIG. 11 also shows the enhanced blockage-device interface.

DETAILED DESCRIPTION OF THE INVENTION

Figure 1:
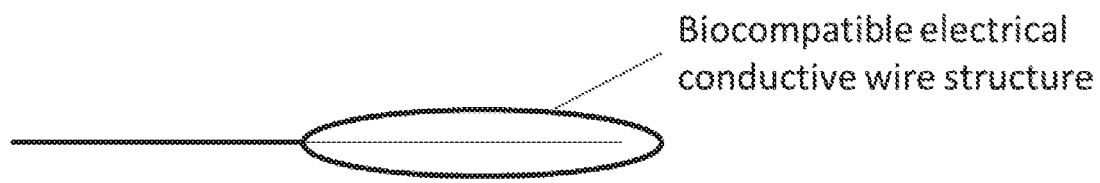
FIG. 1 shows a schematic drawing of the claimed device being a biocompatible conductive wire structure.
Figure 2:
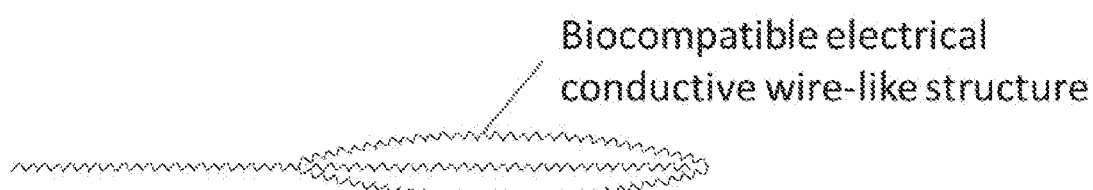
FIG. 2 shows a schematic drawing of an embodiment of the claimed device being a biocompatible conductive structure.
Figure 3:
FIG. 3 shows a schematic drawing of an embodiment of the claimed device being multiple sets of biocompatible conductive structure arranged along the longitudinal direction.
Figure 4:
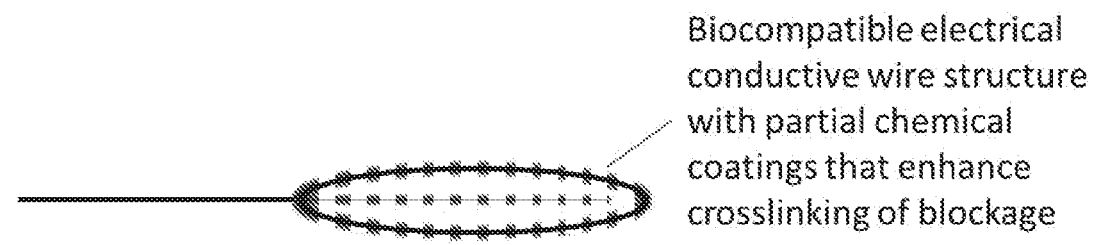
FIG. 4 shows a schematic drawing of an embodiment of the claimed device being coated with one or more chemicals that can enhance cross-linking of the blockage.
Figure 5:
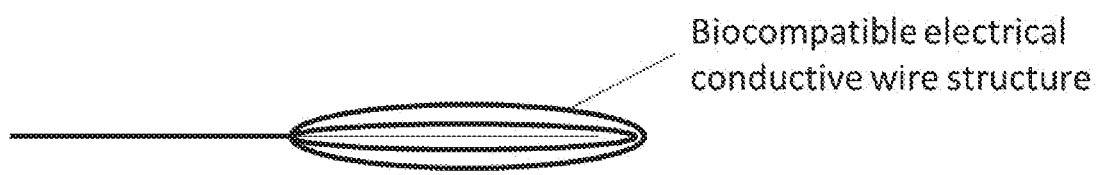
FIG. 5 shows a schematic drawing of an embodiment of the claimed device being multiple sets of biocompatible conductive structure arranged along the radial direction.
Figure 6:
FIG. 6 shows a schematic drawing of two or more terminal ends of an embodiment of the claimed device connected to an electrical power source.
Figure 7:
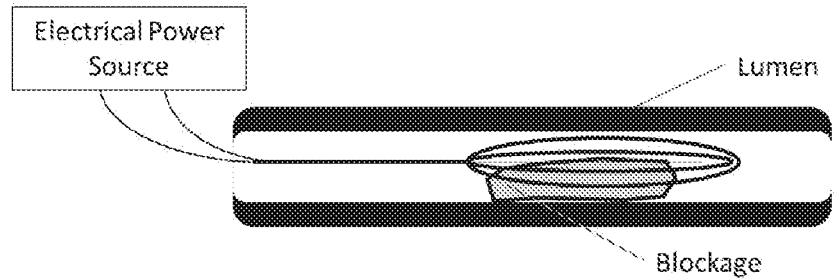
FIG. 7 shows a schematic drawing of a situation where an embodiment of the claimed device is deployed in a lumen in partial contact with a blockage.
Figure 8:
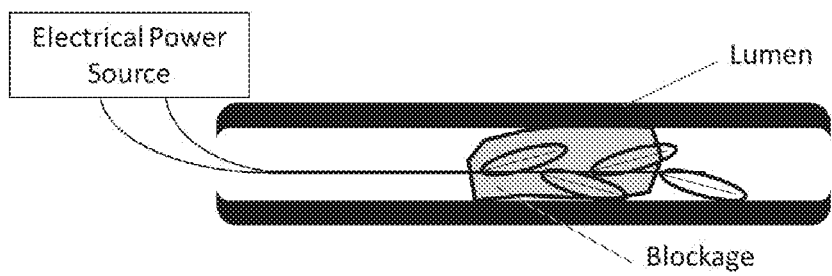
FIG. 8 shows a schematic drawing of a situation where an embodiment of the claimed device is deployed in a lumen and the structure of the device is in contact with the blockage.
Figure 9:
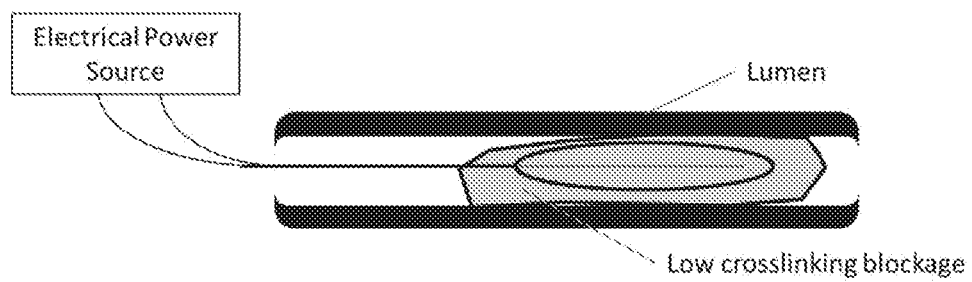
FIG. 9 shows a schematic drawing of a situation prior to application of RF where an embodiment of the claimed device is deployed in a lumen and the structure of the device is in contact with the blockage. This figure also shows that structure should contact the blockage when deployed in lumen.
Figure 10:
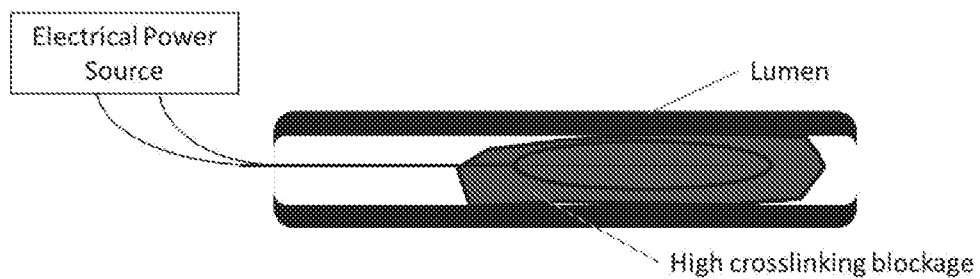
FIG. 10 shows a schematic drawing of an embodiment of the claimed device after the application of RF induced an increase in cross-linking density of the blockage.
Figure 11:
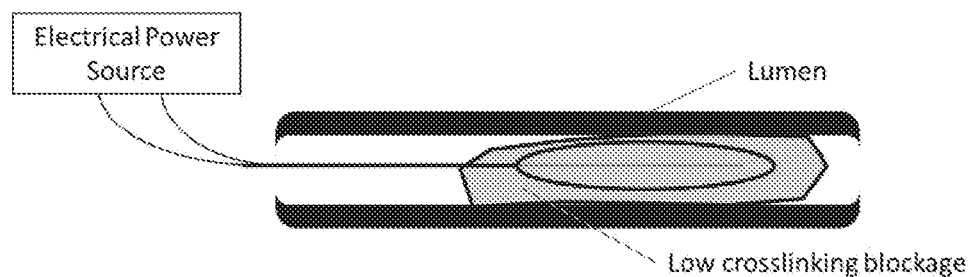
FIG. 11 shows a schematic drawing of an embodiment of the claimed device with increased interfacial adsorption between surface of the structure and a blockage.

The present invention provides a RF electro-thrombectomy device for removal of vascular lumen blockages with a low risk of vessel wall damage and blockage fragmentation due to the use of RF electric current to strengthen the blockage and the blockage-device interface prior to blockage removal. The blockage removal device of the present invention causes an electric current, such as RF or direct electric current, to pass through a blockage, which lumen blockage can be, but are not limited to, a thrombus, blood clot or embolus.

Embodiments of the RF electro-thrombectomy device are generally made of electrically conductive and optionally biocompatible, conducting wires, manipulation wire, and a structure that is designed to capture a vascular blockage, connected to an RF system. An RF system generates an RF electric current. A preferred embodiment of the RF electro-thrombectomy device comprises at least one biocompatible, manipulation wire and a structure. In some embodiments, the RF electro-thrombectomy device comprises multiple sets of manipulation wires having one or more structures arranged along the longitudinal direction of the manipulation wire. In other embodiments, the RF electro-thrombectomy device of the present invention comprises multiple sets of biocompatible manipulation wires or structures arranged along the radial direction. In some embodiments, the structure is elliptical in shape. In other embodiments, the structure comprises a bundle of wires. In some embodiments, the structure comprises multiple sets of elliptical shapes and is uniformly arranged in the axial direction, for example, of a manipulation wire. In other embodiments, the structure comprises multiple sets of wires or bundles of wires that are uniformly arranged in the radial direction of the manipulation wire. In preferred embodiments of the device, the structure is a set of at least two wires that are in contact with a blockage when deployed. In a device comprises multiple manipulation wires and multiple structures, different sets of manipulation wires and structures may not be electrically connected with other, such that electrical potential different between the manipulation wires or the structures will build up if they are connected to a power source.

A manipulation wire refers to an element of the device which is designed to introduce and manipulate the structure that is designed to capture the blockage into a lumen of a vascular structure. Typically, a manipulation wire is flexible and thin, which provides that the manipulation wire can be easily maneuvered to introduce the structure that is designed to capture the blockage into the lumen of a vascular structure. In one embodiment, the manipulation wire is braided. In certain embodiments the manipulation wire is a combination of two or more wires.

The structure designed to capture the blockage is present at an end of the manipulation wire and is appropriately shaped so that the structure captures the blockage with sufficient strength to pull the blockage out of the vascular lumen by pulling the manipulation wire. In certain embodiments, the structure designed to capture the blockage comprises one or more oval, elliptical, triangular, square, or rectangular units. In one embodiment, the structure is a mesh. In a further embodiment, the structure is self-expandable, i.e., the structure is packed in a smaller structure in a manner that expands into a larger expanded structure, for example, by a spring action of the structure. A person of ordinary skill in the art can design additional structures that can capture a blockage from a lumen of a vasculature and such embodiments are within the purview of the invention.

In preferred embodiments, when the manipulation wire and the structure of the RF electro-thrombectomy device are deployed in the lumen, the structure is in fill or partial contact with the blockage. When the electrical circuit is closed, the RE electric current conducts through the manipulation wire, structure, blockage and electric power source. The electric current conducted by the RF electro-thrombectomy device that passes through the blockage can increase the cross-linking density of components of the blockage, such as proteins and fibrin. The RF electro-thrombectomy device conducts RF electric current through the entire blockage so that the strengthening is more uniformly distributed without significant risk of damage to any vascular structures. The increased cross-linking density of the components of the blockages increases the fracture resistance of the blockage and the adsorption of components of the blockage, such as proteins in the blockage, onto the device. Upon increased adsorption of the components of the blockage onto the device, the interfacial fracture resistance between the device and the blockage is increased, which allows retraction and removal of the device and the adherent blockage using conventional catheter and guidewire systems. Because the electric current conducted by the device to pass through the blockage increases the cross-linking density of components of the blockage and makes the blockage more fracture resistant, the structure-adherent blockage can be moved with the structure through a vessel and the blockage can be retrieved with minimal or no fragmentation of blockage material during the retrieval procedure.

In certain embodiments, the electrically conductive material of the RE thrombectomy device can transmit RF electric current. In preferred embodiments, the manipulation wire or structure of the device are made of electrically conductive material that can transmit electric current, for example, an alternating current (AC) or a direct current (DC). When the device is in use, electric current passes through the blockage. The electric current applied to the blockage can be in a sinusoidal from, a continuous from, or a step form.

In certain embodiments, the manipulation wire and/or structures are self-expandable. The self-expandable manipulation wire and/or structures can be stowed in and deployed from a catheter to a position in the lumen of a blood vessel.

The RF electro-thrombectomy device is suitable for use in retrieval tolerant vasculature, i.e. blood vessels that allow the retrieval of blood clots, and for the retrieval of fresh and aged thrombi, i.e. thrombi with more fully developed fibrin meshworks. The device of the present invention minimizes vascular damage observed with other thrombectomy devices by reducing radially applied force on the inner lumen surface. Advantageously, RF electric current applied by the device of the present invention can increase the fracture resistance of the whole blockage to resist fragmentation and embolization of fragmented blockage material. Enhanced adhesion between the device and the blockage reduces blockage loosening during retrieval and inhibits tertiary occlusion. The combined bulk strengthening and interfacial adhesion strengthening reduce tertiary occlusion from fragmentations without the need of high radial force for blockage-capture, which can damage the vessel wall.

In certain embodiments, the device comprises more than one set of manipulation wire and structure and at least one set of the manipulation wire or structure is made from electrically conductive material and can be deployed from a catheter to a non-vascular lumen of an organ or body cavity. In preferred embodiments, the manipulation wire and structure of the RF electro-thrombectomy device to be employed in a non-vascular lumen of an organ or body cavity is of sufficient size to pass through and/or past the entire blockage in such organ lumen or cavity. In alternative embodiments, the manipulation wire and structure of the RF electro-thrombectomy device is of sufficient size to pass partially through or past the blockage in the organ lumen or cavity. In some embodiments, the RF electric current to be applied to a blockage in an organ lumen or cavity can be higher than the RF electric current applied in a RF electro-thrombectomy device employed in a vascular lumen. In certain embodiments, where the blockage is of a size that cannot be completely passed by the RF electro-thrombectomy device, the blockage can be partially passed, partially adhered to the device, and the device and the adherent partial blockage can be retrieved. In some embodiments, where the manipulation wire and structure of the RF electro-thrombectomy device is employed to completely or partially retrieve a blockage from an organ lumen or cavity, a higher electric current and/or a RF electro-thrombectomy device coated with additional chemical cross-linking enhancers can be applied. It is contemplated that, when the manipulation wire and structure of the RF electro-thrombectomy device is employed in an organ lumen or cavity, partial adherence of the blockage to the device and stepwise partial retrieval of the adherent blockage is feasible, because the risk of embolization of blockage material in organ lumens or cavities is generally less detrimental than embolization in vascular lumens.

In certain embodiments of the present invention, the set of the manipulation wire and structure of the device can be coated or partially coated with chemicals that enhance the cross-linking of a blockage. Chemicals useful in the RF electronic-thrombectomy device, such as chemicals that enhance the cross-linking of components of vessel blockages, are known in the art and include but are not limited to 3-deoxyglucosone, transglutaminase, kynurenine (Kyn), 3-Hydroxykynurenine (3OHKyn), 3-Hydroxykynurenine O-β-D glucoside (3OHKG), 4-(2-amino-3-hydroxyphenyl)-

2-hydroxy-4-oxobutanoic acid O-ρ-D-glucoside (3-OHKG-W), 3-hydroxykynurenine O-β-D-glucoside yellow (3-OHKG-Y), and 2-amino-3-hydroxyacetophenone O-β-D-glucoside (AHAG); and α-dicarbonyl compounds including but not limited to glyoxal, methylglyoxal, 1,3-deoxyosones 1,4-dideoxyosones, and diacetyl. Compounds including Kyn, 3OHKyn, 3OHKG, 3OHKG-W, 3OHLG-Y and AHAG are generally known as UV filters found in the lenses of primates. For example, Kyn, 3OHKyn, and 3OHKG spontaneously deaminate at physiological pH to form highly reactive α,β-ketoalkene intermediates capable of undergoing addition to cysteine, and to a lesser extent histidine and lysine residues, in proteins. Alpha-dicarbonyl compounds modify proteins at physiological conditions with increasing modification with increasing temperatures. In some embodiments, the manipulation wire and structure of the RF electro-thrombectomy device are fully or partially coated with one or more of the UV filter compounds or α-dicarbonyl compounds to enhance protein cross-linking density of components of the blockage, blockage fracture resistance, and adsorption of the blockage to the surfaces of the wires and wire-like structures of the device. To effectuate efficient increases in cross-linking density of blockage components using, for example, α-dicarbonyl compounds applied in the manipulation wire and structure coating, heat generated by the RF electric current can aid protein modification and accelerate the cross-linking process.

Proteins of the coagulation cascade can also be coated onto the manipulation wire and structure of the RF electro-thrombectomy device. For example, plasma factor XIII can be used in the present invention. Factor XIII is a transglutaminase that can be activated non-proteolytically with high monovalent/divalent cations along with low concentrations of calcium. The coating of the manipulation wire and structure can include dimers of A-subunits of factor XIII, which subunits are devoid of the A-subunit activation peptides, and monovalent/divalent cations and low concentrations of calcium. Upon activation of the RF electric current sufficient to induce release of contents of the wire coating, including factor XIII A-subunits, monovalent/divalent cations and low concentrations of calcium, but not high enough to denature factor XIII subunits leads to the local activation of factor XIII transglutaminase activity, which transglutaminase activity aids in increasing the cross-linking density of components of the blockage. In further steps, RF electric currents can be applied, which currents are of sufficient frequencies to further increase the cross-linking density of components of the blockage and denature factor XIII to limit its activity.

The present invention further provides a method for increasing fracture resistance of a lumen blockage comprising navigating the manipulation wire and structure of to a site of occlusion; placing the structure in contact with the blockage; applying an RF or direct electric current through the structure; and retrieving the blockage.

Example—Thrombus Removal

A device with wire structure made of Nitinol and connected to a radio frequency (RF) system, for example, a RF system that provides a current of 200 kHz, is being navigated to a blood vessel blocked by a thrombus. The manipulation wire and structure of the device is deployed across the thrombus using standard surgical technique. The RF system is then connected to a power source. RF electric current is applied to blockage to induce cross-linking of the contents in the thrombus. The thrombus is then retrieved together with the structure.

When employed in an in vitro occlusion model, the manipulation wire and structure of the RF electro-thrombectomy device of the present invention allowed a 100% thrombus retrieval rate, confirming the minimal risk of distal embolization.

What is claimed is:

1. A method of removing a blockage from a vascular lumen, the method comprising the steps of
   a) cross-linking a blockage in a vascular lumen using radio frequency by contacting the blockage with at least two wires made of electrically conductive material and applying a field or current that passes through the entire blockage to increase the cross-linking density of the entire blockage in a substantially uniform manner, and
   b) capturing and removing the cross-linked blockage from the vascular lumen.

2. The method of claim 1, wherein the radio frequency field or current is deployed from a RF-system or an electrical power source outside a body that comprises the vascular lumen.

3. The method of claim 1, wherein the blockage is a thrombus, blood clot, or embolus.

4. The method of claim 1, wherein the field or current is passed in a sinusoidal form, a continuous form, or a step form.

5. The method of claim 2, wherein the cross-linked blockage is removed from the vascular lumen retrograde through a catheter.

* * * * *